(12) United States Patent
Kokkaliaris et al.

(10) Patent No.: US 7,281,847 B2
(45) Date of Patent: Oct. 16, 2007

(54) IMAGE SENSOR FOR DENTAL INTRAORAL RADIOGRAPHY

(75) Inventors: Stelios Kokkaliaris, Merate (IT); Luciano Langella, Como (IT)

(73) Assignee: Gendex Corporation, Washington, DC (US)

( * ) Notice: Subject to any disclaimer, the term of this patent is extended or adjusted under 35 U.S.C. 154(b) by 113 days.

(21) Appl. No.: 11/196,172

(22) Filed: Aug. 3, 2005

(65) Prior Publication Data

US 2006/0028546 A1    Feb. 9, 2006

(30) Foreign Application Priority Data

Aug. 6, 2004    (EP)    ................... 04018748

(51) Int. Cl.
*H01J 31/49*    (2006.01)
(52) U.S. Cl. ................ 378/189; 378/191; 378/205
(58) Field of Classification Search ............. 378/98.8, 378/167, 168, 189, 191, 205; 250/370.09
See application file for complete search history.

(56) References Cited

U.S. PATENT DOCUMENTS

| 5,434,418 A | 7/1995 | Schick |
| 5,510,623 A | 4/1996 | Sayag et al. |
| 5,513,252 A | 4/1996 | Blaschka et al. |
| 5,677,537 A | 10/1997 | Pfeiffer |
| 5,691,539 A | 11/1997 | Pfeiffer |
| 5,694,448 A | 12/1997 | Morcom |
| 5,884,129 A | 3/1999 | Ichimura et al. |
| 6,030,119 A * | 2/2000 | Tachibana et al. .......... 378/169 |
| 6,169,781 B1 | 1/2001 | Doebert et al. |
| 6,343,875 B1 | 2/2002 | Eppinger et al. |
| 6,905,244 B2 * | 6/2005 | Kilcher et al. .............. 378/170 |
| 2004/0096040 A1 | 5/2004 | Kilcher et al. |

FOREIGN PATENT DOCUMENTS

EP    1 330 982    7/2003

* cited by examiner

*Primary Examiner*—Jurie Yun
(74) *Attorney, Agent, or Firm*—McNees Wallace & Nurick LLC

(57) ABSTRACT

An image sensor (10) for dental intraoral radiography comprises a housing (12), an image receptor (40) and a cable connection dome (32) arranged on a back side (14) of the housing (12). The back side (14) of the housing (12) has a depression (36) at least in the region between the cable connection dome (32) and an anterior side (16) of the housing (12), wherein the depression (36) falls short of reaching the anterior side (16) of the housing (12) such that an elevated region (38) is formed between the depression (36) and at least the anterior side (16) of the housing (12). A positioning device (50) is adapted for positioning an image sensor (10) according to the present invention in the mouth of a patient. The present invention provides an intraoral sensor that enables good patient cooperation, thus making it possible to take high quality dental x-ray images.

20 Claims, 3 Drawing Sheets

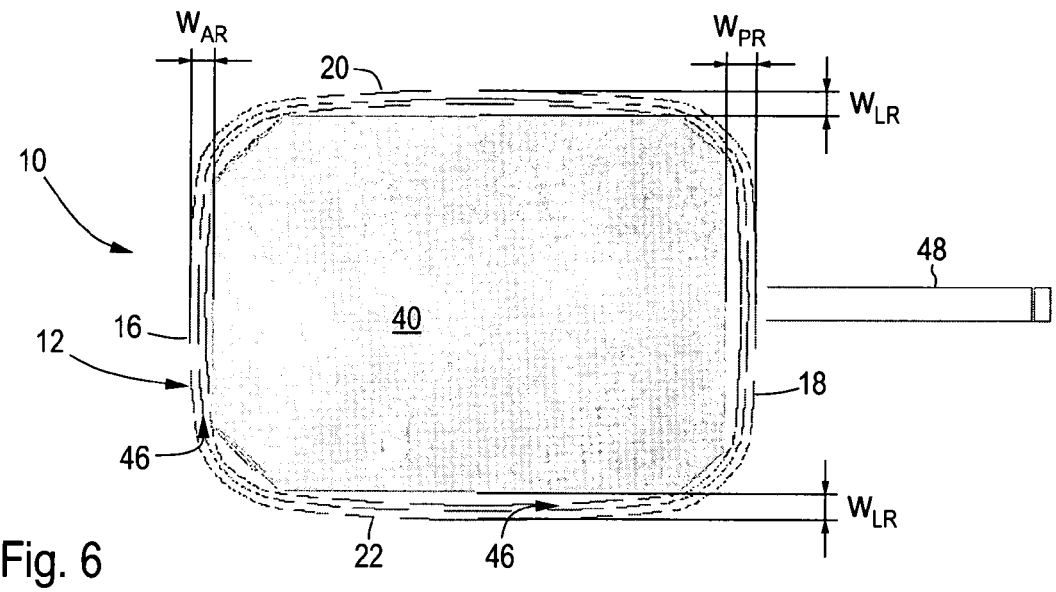
Fig. 6
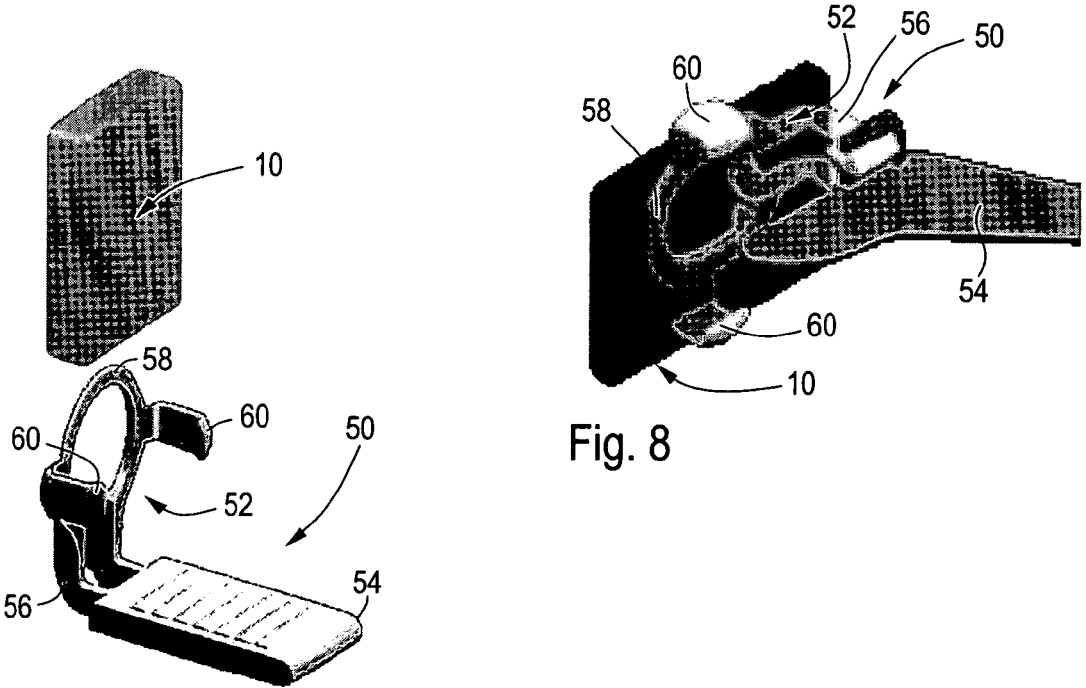
Fig. 7
Fig. 8

IMAGE SENSOR FOR DENTAL INTRAORAL RADIOGRAPHY

BACKGROUND OF THE INVENTION

The present invention concerns the field of intraoral sensors for taking x-ray images.

The first electronic intraoral x-ray image sensors have been commercialized approximately in 1990. These sensors are intended to be placed in the mouth of a patient to produce an x-ray image of the teeth and/or the jaw. The sensor typically comprises an electronic image receptor having an active imaging area. The receptor is encapsulated and protected by a housing, which may be composed of plastic and/or metal elements. Image sensors of this type of construction have rapidly gained market share over the traditional method of using photographic film because the electronic x-ray image is immediately available and can be enhanced on a computer using sophisticated imaging software.

Typical dental applications of such image sensors are the acquisition of so-called "periapical" and "bite-wings" images. In order to take a periapical image, the sensor is positioned vertically with its anterior side tightly close to the zone where the tooth apex is located. For bite-wings images, the sensor is positioned with its anterior side deeply inserted into the mouth of the patient to capture both the upper and lower crowns of the teeth. The patient is asked to close his or her mouth as much as possible, thus bringing the lateral side of the sensor in contact with the palatal and lingual surfaces (i.e., the "the ceiling" and "floor") of the mouth of the patient. It is important that the patient is able to close his or her mouth as much as possible in order to obtain a maximum image area.

U.S. Pat. No. 6,169,781 discloses an image sensor with an approximately rectangular housing. The anterior side of the housing is rounded in a way that is adapted to the anatomical characteristics of the upper jaw of the average patient. A smoothing or indentation with a relatively large radius is formed on the back side of the housing between a cable connection dome and the anterior side of the housing. The indentation reaches up to the anterior side of the housing so that the housing is thinner at its anterior side than it is at its posterior side.

U.S. Pat. No. 5,691,539 discloses an intraoral sensing device with a rounded, octagonal shaped housing.

U.S. Pat. No. 5,510,623 discloses a solid state CCD image receptor having an octagonal shape. This document also discloses a sensor package with an octagonal shaped housing. The housing comprises a cable connection dome that extends up to the anterior side of the sensor.

The design of a dental image sensor is a difficult task. On the one hand, the inactive rims between the electronic image receptor and the outer side of the housing should be as small as possible, thus allowing to capture as much as possible of the subject of interest within in the active imaging area. The thinner the inactive rim is (mainly with respect to the lateral side for bite-wings images and mainly with respect to the anterior side for periapical images), the more of the subject will be captured within the imaging area. On the other hand, it is important that the sensor has a rounded, comfortable housing so that the patient will cooperate and close his or her mouth around the sensor as much as possible. This is especially important when the patient is a child or tends to overreact or has a marked gag reflex or has an easily irritable oral anatomy.

In solving the above problems, not only the sensor itself must be considered, but also the overall assembly when the sensor is inserted into a holder or positioning device. This whole assembly should easily fit into the patient's mouth, creating as little discomfort or irritation as possible while at the same time allowing the capture of high-quality images of the desired region.

SUMMARY OF THE INVENTION

The present invention has the object of solving the above problems at least in part. In particular, the intraoral sensor of the present invention should enable good patient cooperation, thus making it possible to take high quality images even if the sensor is inserted into a holder or positioning device. According to preferred embodiments of the invention, the sensor should also allow an active imaging area that is close to the outer sides of the sensor.

The invention is based on the idea to provide the back side of the housing of the image sensor with a depression that falls short of reaching the anterior side of the housing such that an elevated region is formed between the depression and at least the anterior side of the housing. This unique shape offers a number of substantial advantages. The elevated region makes it possible to combine a relatively large edge rounding radius with a relatively small width of an inactive rim between the outer perimeter of the housing and the internal image receptor. Furthermore, the elevated region increases the mechanical robustness of the housing. Yet further, the depression and/or the elevated region can be used to provide a particularly good fit of the image sensor in a positioning device such that the amount that a holder basket of the positioning device must protrude over the outer contours of the image sensor is as small as possible.

In preferred embodiments, the elevated region extends from the anterior side of the sensor along the full length of the lateral sides to the posterior corners of the housing. Correspondingly, the depression may surround the cable connection dome fully—i.e., by an angle of 360°—or at least in part—e.g., by an angle of more than 180° or more than 270°.

A large edge rounding radius is important since it reduces the pressure against the inner surfaces of the mouth of the patient and also provides a comfortable visual appearance of the sensor. Both of these factors contribute to achieving good patient cooperation. In preferred embodiments, the edge rounding radius is at least 2 mm and preferably at least 3 mm. In a number of embodiments, this edge radius may be present only at the anterior side of the housing or at the anterior and the lateral sides of the housing or at all sides of the housing.

Another factor for obtaining a smooth and comfortable shape of the image sensor is the rounding of the anterior and posterior corners. In a preferred embodiment, the corner radius is 2.5 mm-15 mm. The corner rounding may be asymmetrical in some embodiments, with the anterior corners being more chamfered than the posterior corners.

In order to obtain a maximum usable image area, the width of the inactive rim of the image sensor should be small, e.g., at most 4 mm and preferably at most 2.5 mm. In a number of embodiments, this width may be present only at the anterior side of the housing or at the anterior and the lateral sides of the housing or at all sides of the housing.

BRIEF DESCRIPTION OF THE DRAWINGS

Further features, objects and advantages of the present invention will be apparent from the following detailed description of a sample embodiment and several alternative embodiments. Reference is made to the accompanying drawings, in which:

FIG. 6 shows a view onto the front side of the sensor of FIG. 1 wherein the position and shape of an embedded image receptor is shown, FIG. 7 shows a perspective, drawn-apart view of an assembly that comprises a sensor and a positioning device according to the present invention, and FIG. 8 shows a perspective view of an assembly that comprises a sensor and an alternative positioning device according to the present invention. Wherever possible, the same reference numbers will be used throughout the drawings to refer to the same or like parts.

DETAILED DESCRIPTION OF THE INVENTION

Figure 1:
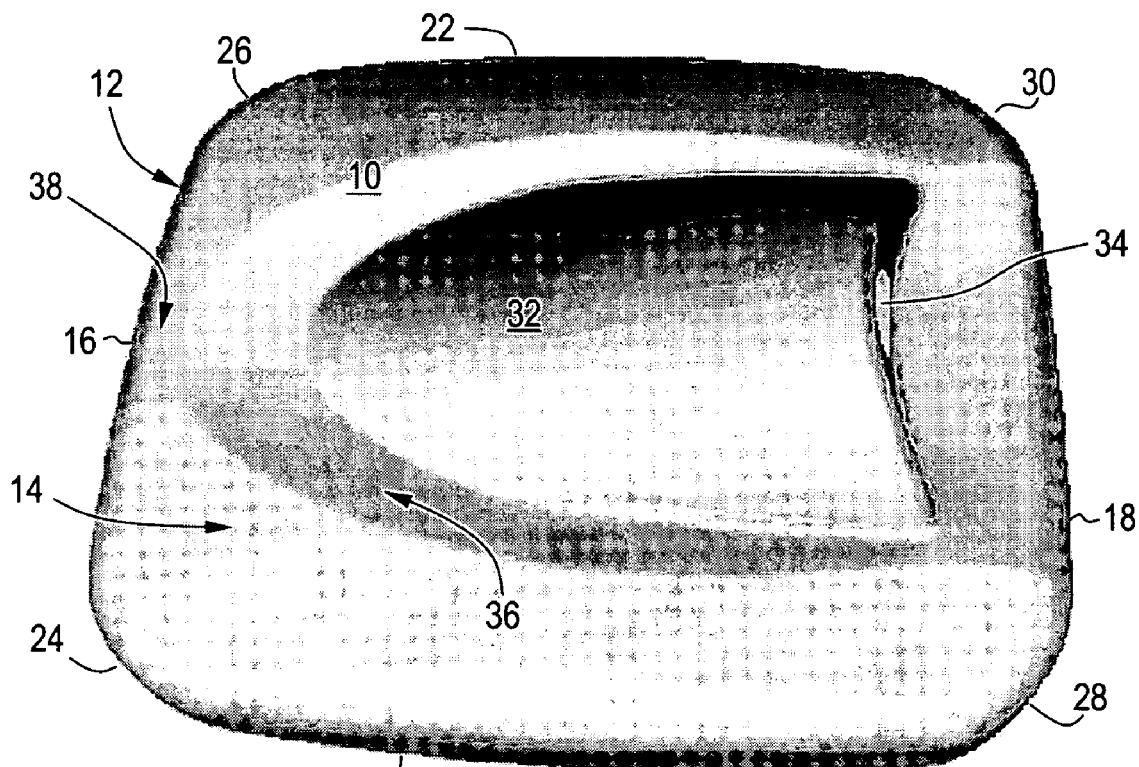
FIG. 1 shows a perspective view of the back side of a sensor according to the present invention.

The dental image sensor 10 shown in FIG. 1 comprises a housing 12 that encapsulates an image receptor (not shown). FIG. 1 depicts a back side 14 of the housing 12, i.e., the side that is opposite to a front side (not shown). The housing 12 has an anterior side 16, a posterior side 18 and two lateral sides 20, 22. The anterior side 16 merges into the lateral sides 20, 22 at two anterior corners 24, 26. Likewise, the posterior side 18 merges into the lateral sides 20, 22 at two posterior corners 28, 30.

The back side 14 of the housing 12 has an approximately central, elongated, spade-shaped cable connection dome 32. The cable connection dome 32 comprises a cable outlet 34 that is arranged on a steep wall of the cable connection dome 32 facing towards the posterior side 18. A cable (not shown) exits the housing 12 at the cable outlet 34. The cable serves for supplying the image sensor 10 with electricity and for transmitting image information obtained by the image sensor 10 to an external computer (not shown). The cable may be permanently fixed to the image sensor 10, or it may be removable at the cable outlet 34.

The back side 14 of the housing 12 further comprises a depression 36 that, in the present sample embodiment, surrounds the cable connection dome 32 at all sides. The depression 36 seamlessly merges into the posterior side 18. However, the depression 36 does not reach the anterior side 16 and the lateral sides 20 and 22. The back side 14 therefore has an elevated region 38 between the anterior side 16 and the depression 36, and this elevated region 38 further extends laterally along the full length of the image sensor 10 towards the posterior corners 28, 30. In other words, the elevated region 38 is not only arranged between the depression 36 and the anterior side 16, but also between the depression 36 and the lateral sides 20 and 22. The back side 14 of the housing 12 is essentially flat over the entire elevated region 38.

Figure 2:
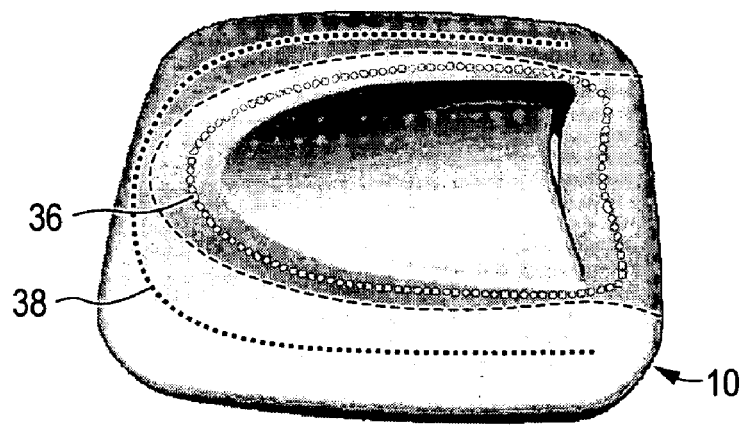
FIG. 2 shows the view of FIG. 1 at a reduced scale, wherein an elevated region and a depression in a housing of the sensor have been marked.

In FIG. 2, the general extension of the depression 36 has been marked by white square dots. The elevated region 38 is has been marked by black square dots, and the boundary between the depression 36 and the elevated region 38 has been marked by a thin dashed line.

Figure 3:
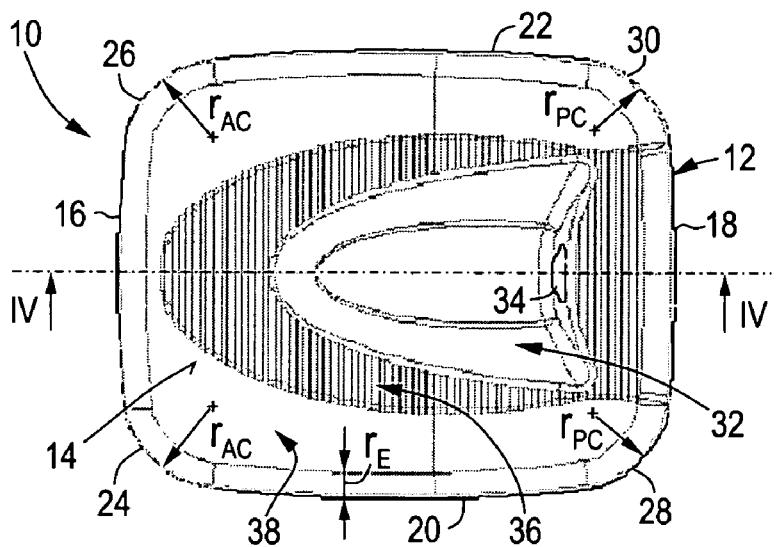
FIG. 3 shows a line drawing of the back side of the sensor of FIG. 1.

FIG. 3 again depicts the features that have been discussed above. The extent of the depression 36 has been marked by a hatching with vertical hatching lines. FIG. 3 further shows that the edges between the back side 14 and the anterior, posterior and lateral sides 16, 18, 20, 22 are rounded with an edge rounding radius $r_E$ to enhance the patient comfort. In the present sample embodiment, the edge rounding radius $r_E$ is approximately equal in every direction, and it is at least 3 mm. The same edge rounding with the same edge rounding radius $r_E$ is also present at the edge between the front side of the housing 12 and the anterior, posterior and lateral sides 16, 18, 20, 22. Different or non-uniform edge rounding radii may be used in alternative embodiments of the invention.

FIG. 3 further depicts the rounding of the sensor at the anterior corners 24, 26. This rounding is approximately (but not exactly) circular, with an anterior corner rounding radius $r_{AC}$. A corresponding rounding exists at the posterior corners 28, 30 with a posterior corner rounding radius $r_{PC}$.

In the present sample embodiment, the corners 24-30 are rounded in an asymmetric way to fit comfortably into the closed mouth of a patient. More particularly, the two anterior corners 24, 26 (which are generally inserted more deeply into the mouth of the patient) are chamfered more than the posterior corners 28, 30. However, there is still a considerable rounding of the posterior corners 28, 30 to allow an easy positioning of the sensor in the mouth of the patient as close as possible to the teeth, and to reduce the discomfort of the patient when the sensor is put vertically for taking a periapical image.

In the present sample embodiment, the rounding radius $r_{AC}$ of the anterior corners 24, 26 is approximately 7 mm-10 mm, while the rounding radius $r_{PC}$ of the posterior corners 28, 30 is less by about 10%-30%. As mentioned above, these numbers are only approximate since the actual shape of the corners 24-30 in the present sample embodiment is not exactly circular, but slightly elliptical.

Figure 4:
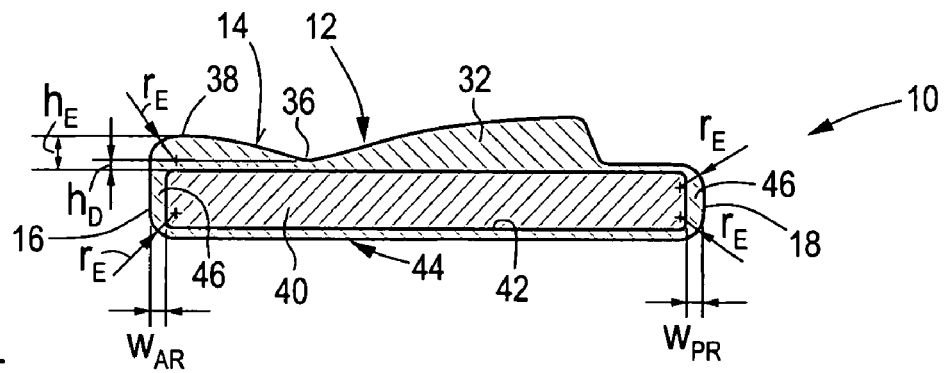
FIG. 4 shows a schematic sectional drawing along the line IV-IV of FIG. 3.

The sectional diagram of FIG. 4 shows the housing 12 as well as the image receptor 40, which is embedded within the housing 12. The image receptor 40 may, e.g., be a CCD or CMOS electronic device, which is coated or coupled with an intensifying screen. The image receptor 40 comprises an active imaging area 42, i.e., the area where the image is actually produced if x-ray radiation is received. The active imaging area 42 is directed towards the front side of the housing 12; in FIG. 4, this front side is marked by reference numeral 44. The image receptor 40 as such is commercially available and may, for example, be of the type shown in U.S. Pat. No. 5,510,623.

The housing 12 may be made generally from plastic or generally from metal, or it may be a hybrid housing comprising both plastic and metal parts. Since the housing 12 encapsulates the image receptor 40 at all sides, an inactive rim 46 is formed around the active imaging area 42. FIG. 4 shows the width $w_{AR}$ of the inactive rim 46 at the anterior side 16 and the width $w_{PR}$ of the inactive rim 46 at the posterior side 18. In the present sample embodiment, the anterior rim width $w_{AR}$ is at most 2.5 mm while the posterior rim width $w_{PR}$ is slightly larger.

FIG. 4 further shows the thickness or height of the housing 12 at its back side 14, as measured against the back side of the embedded image receptor 40. The maximum height at the elevated region 38 is termed $h_E$, while the minimum height at the depression 36 is termed $h_D$. In the present embodiment, the height $h_D$ is approximately 0.5 mm-3 mm, while the height $h_E$ is larger than $h_D$ by at least 30% and preferably by at least 100%.

It is further apparent from FIG. 4 that—at the sectional plane depicted there—the overall thickness of the image sensor 10, i.e., the distance between the front side 44 and the back side 14, is more at the anterior side 16 than it is at the posterior side 18. This is because, in the present sample embodiment, the depression 36 reaches all the way from the cable connection dome 32 to the posterior side 18 without any intervening elevated region. This provides sufficient space to lead the cable that exits from the cable outlet 34 away from the image sensor 10 without creating an additional disturbance for the patient.

Figure 5:
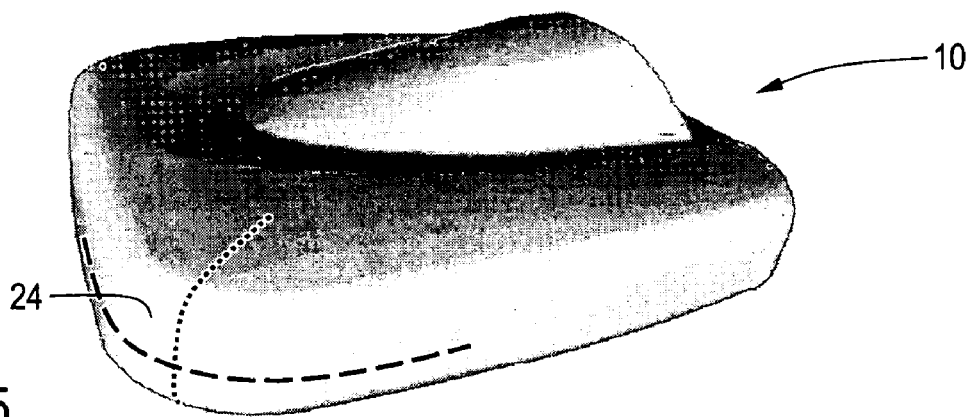
FIG. 5 shows a shaded perspective view of the sensor of FIG. 1 in a different angle of view wherein an anterior corner points towards the viewer.

FIG. 5 shows the smooth and comfortable look of the image sensor 10, which is caused by its general rounding of all edges and corners in all directions. The dotted line in FIG. 5 demonstrates the rounding of the edges with the edge rounding radius $r_E$ at the anterior corner 24, while the dashed line demonstrates the rounding of the corner 24 with the anterior corner rounding radius $r_{AC}$.

It is a merit of the inventors of the present invention to have realized that the smooth and comfortable appearance of the image sensor 10 is an important aspect that has not fully been taken into account in the prior art. In order to obtain cooperation of the patient when introducing the image sensor 10 into the patient's mouth, the image sensor 10 must first of all appear to be comfortable, and not offensive nor pain promising. The comfort of the patient begins with the perception of comfort. Therefore the edges of the housing 12 are rounded in every direction with the comparatively large edge rounding radius $r_E$ of at least 3 mm in the present sample embodiment. This rounded shape may lead to a slightly larger overall thickness of the image sensor 10 than would otherwise be possible. However, it has been found that the increase in acceptability to the patients actually makes the image sensor 10 more usable and in the end results in better quality medical images.

FIG. 6 depicts the outer contours of the housing 12 with the embedded image receptor 40. The cable that connects the image sensor 10 to an external processing unit (not shown) is designated with reference numeral 48.

It is apparent from FIG. 6 that the image receptor 40 has an octagonal shape, thus achieving a good fill-factor of the housing 12. In contrast thereto, the use of a rectangular shaped image receptor encapsulated in a rounded housing would lead to an inefficient fill-factor and a large inactive rim. The octagonal image receptor 40 of the present sample embodiment is especially well adapted to the asymmetrical shape of the housing 12 since the anterior corners of the image receptor 40 are "cut away" to a larger extent than its posterior corners. The good fill-factor of the image receptor 40 of the present sample embodiment again means high patient comfort since the active imaging area 42 of the image receptor 40 may be closer to the outer perimeter of the housing 12, especially at the anterior side 16 and at the lateral sides 20, 22.

In the present sample embodiment, the anterior rim width $w_{AR}$ is approximately 2.5 mm or less. The width $w_{LR}$ of the inactive rim 46 at the lateral sides 20, 22 is approximately equal to the anterior rim width $w_{AR}$, i.e., 2.5 mm. These narrow rim widths at the anterior and lateral sides 16, 20, 22 enable a close positioning of the active imaging area 42 against the subject of the x-ray investigation. The posterior rim width $w_{PR}$ is not so critical, and it can be increased if more mechanical stability is desired or if additional room within the housing 12 is needed for electronic components and cable connections. In the present sample embodiment, the posterior rim width $w_{PR}$ is approximately 4 mm.

Returning to FIG. 4, it is apparent that a housing 12 which has a minimal height over the whole area of the back side 14 would be sufficient for the purpose of encapsulating the image receptor 40. At the first glance, the additional volume of the elevated region 38 up to the height $h_E$ would therefore appear to be "wasted". However, the elevated region 38 makes it possible to combine a relatively large edge rounding radius $r_E$ with a relatively small anterior rim width $w_{AR}$. The large edge rounding radius $r_E$ is important since a smaller radius would create a narrower curvature and thus a less comfortable edge pressing against the inner surfaces of the mouth of the patient.

Moreover, thin anterior and lateral rim widths $w_{AR}$ and $w_{LR}$ around the image receptor 40 have the consequence that there is only little protection of the image receptor 40 against mechanical shocks and pressure. The rounded elevated region 38, which stretches from the anterior side 16 along both lateral sides 20, 22 up to both posterior corners 28, 30, increases the robustness of the housing against compression and shocks, thus compensating the relative thinness of the inactive rim 46.

The elevated region 38—and the depression 36 defined thereby—serve for another important purpose, which will be explained in the following with reference to FIG. 7 and FIG. 8.

An intraoral image sensor like the sensor 10 of the present invention needs to be positioned in the mouth of the patient with the help of an aiming or holding or positioning device like the positioning device 50 shown in FIG. 7. The positioning device 50 assures the correct geometry of exposure, i.e., orthogonality between the x-ray beam and the active imaging area 42 of the image sensor 10. However, every additional object inserted into the mouth of the patient during dental treatment increases the patient's discomfort. In general, this problem becomes the more severe the more the positioning device 50 increases the outer dimensions of the image sensor 10.

The positioning device 50 as shown in FIG. 7 comprises a basket 52 and a bite block 54. The basket 52 and the bite block 54 may be formed by one integral piece of plastic, or alternatively the basket 52 and the bite block 54 may be separate pieces that are removably attached to each other.

The basket 52 comprises a connecting portion 56, a holding member 58 and two side brackets 60. The connecting portion 56 has a 90° bend and joins the holding member 58 to the bite block 54. The holding member 58 and the side brackets 60 of the basket 52 are adapted to receive the image sensor 10. In the present sample embodiments, the holding member 58 has at least one curved portion with an approximately annular or elliptical shape.

The holding member 58 is formed so that it engages with both the cable connection dome 32 and the elevated region 38 of the image sensor 10 when the image sensor 10 is inserted into the basket 52. In this position, the holding member 58 at least partially rests in the depression 36. This has the consequence that the holding member 58 adds little or no thickness to the overall assembly when the image sensor 10 is inserted into the positioning device 50.

Furthermore, the engagement of the holding member 58 with the cable connection dome 32 on one side and with the elevated region 38 on the other side contributes to a good fit of the image sensor 10 in the positioning device 50. The side brackets 60 can therefore be made comparatively thin and small in order to provide a minimum of discomfort for the patient.

In the embodiment of FIG. 7, the side brackets 60 engage the lateral sides 20, 22 of the image sensor 10 at a very small area. The anterior and posterior sides 16, 18 and the corners 24-30 of the sensor 10 are left entirely free. The inventors also contemplate alternative embodiments in which the basket 52 only has side brackets that contact the anterior and/or posterior sides 16, 18 of the sensor 10. For example, one side bracket may reach around the anterior side 16, and two side brackets may be arranged at the posterior side 18, the latter being arranged symmetrically to the cable 48. In such embodiments, both lateral sides 20, 22 and all four corners 24-30 may be left entirely free of any holding elements. It is important in all cases that the positioning device 50 does not add any substantial protrusions to the lateral sides 20, 22 of the sensor 10 since these sides will be in direct contact with the inner surfaces of the patient's mouth when the x-ray image is being taken.

FIG. 8 shows an alternative embodiment of the positioning device 50 into which the image sensor 10 has been inserted. In this embodiment, a removable connection is shown between the basket 52 and the bite block 54, and the respective shapes of the basket 52 and the bite block 54 are different from those shown in FIG. 7. Again, it is apparent that the holding member 58, whose form corresponds to the form of the depression 36, at least partially rests in the depression 36 and engages both the cable connection dome 32 and the elevated region 38. This construction allows for a particularly good fit of the image sensor 10 in the basket 52 and decreases the need for real estate when positioning the complete assembly in the mouth of the patient.

It is to be remarked that the drawings shown in FIG. 7 and FIG. 8 have been created by modifying drawings of positioning devices that are presently manufactured and marketed by Dentsply Rinn, Elgin, Ill., US. No rights are claimed with respect to any elements shown in the drawings that may be proprietary to Dentsply Rinn. The particular feature which the inventors believe to be novel and non-obvious is the construction of a positioning device 50 with a holding member 58 that interacts with the cable connection dome 32 and/or the elevated region 38 and rests at least partially in the depression 36 when a sensor 10 according to the present invention is inserted into the positioning device 50.

Summing up, the image sensor 10 and positioning device 50 as described above feature a comfortable rounded shape without any sharp edges and allow a comfortable positioning of the assembly into the mouth of the patient, optimizing the compromise between the active image area 42 of the sensor 10 and the outer dimensions of the housing 12. Since the image sensor 10 has neither sharp edges nor square corners, it can easily be positioned without causing pain or discomfort to the patient when the patient closes his or her mouth to hold the sensor during the x-ray exposure.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An image sensor for dental intraoral radiography, comprising:
   a housing having a front side, a back side, a posterior side, an anterior side, and two lateral sides;
   an image receptor contained in the housing and exposing an active imaging area towards the front side of the housing for receiving radiation;
   a cable connection dome arranged on the back side of the housing with a cable outlet towards the posterior side of the housing; and
   the back side of the housing has a depression at least in a region between the cable connection dome and the anterior side of the housing, wherein the depression falls short of reaching the anterior side of the housing such that an elevated region is formed between the depression and at least the anterior side of the housing.

2. The image sensor of claim 1, wherein the depression further extends at least to a region between the cable connection dome and the lateral sides of the housing, wherein the depression falls short of reaching the lateral sides of the housing such that the elevated region surrounds the cable connection dome over a sector of more than 180°.

3. The image sensor of claim 2, wherein the depression further extends to the posterior side of the housing and reaches the posterior side of the housing.

4. The image sensor of claim 2 wherein the depression falls short of reaching the lateral sides of the housing such that the elevated region surrounds the cable connection dome over a sector of more than 270°.

5. The image sensor of claim 2 wherein edges of the housing are rounded at least at the anterior and lateral sides with an edge rounding radius of at least 2 mm.

6. The image sensor of claim 2 wherein anterior corners delimiting the anterior side of the housing are rounded with an approximate anterior corner radius, and posterior corners of the housing delimiting the posterior side of the housing are rounded with an approximate posterior corner radius, wherein the anterior corner radius is larger than the posterior corner radius.

7. The image sensor of claim 2 wherein a width of an inactive rim where the housing extends over the area of the image receptor is at most 4 mm at least at the anterior and lateral sides of the housing.

8. The image sensor of claim 2 wherein a minimum height of the housing at the depression, as measured against the back side of the embedded image receptor, is between about 0.5 mm and about 3 mm, and in that the maximum height of the housing at the elevated region, as measured against the back side of the embedded image receptor, is larger than the minimum height by at least 30%.

9. The image sensor of claim 1, wherein edges of the housing are rounded at least at the anterior and lateral sides with an edge rounding radius of at least 2 mm .

10. The image sensor of claim 9 wherein the edges of the housing are rounded at least at the anterior and lateral sides with an edge rounding radius of at least 3 mm.

11. The image sensor of claim 9 wherein a width of an inactive rim where the housing extends over the area of the image receptor is at most 4 mm at least at the anterior and lateral sides of the housing.

12. The image sensor of claim 9 wherein a minimum height of the housing at the depression, as measured against the back side of the embedded image receptor, is between about 0.5 mm and about 3 mm, and in that the maximum height of the housing at the elevated region, as measured against the back side of the embedded image receptor, is larger than the minimum height by at least 30%.

13. The image sensor of claim 1, wherein anterior corners delimiting the anterior side of the housing are rounded with an approximate anterior corner radius, and posterior corners of the housing delimiting the posterior side of the housing are rounded with an approximate posterior corner radius, wherein the anterior corner radius is larger than the posterior corner radius.

14. The image sensor of claim 13, wherein the anterior corner radius is 5 mm-15 mm, and the posterior corner radius is less than the anterior corner radius by 5%-50%.

15. The image sensor of claim 1, wherein a width of an inactive rim where the housing extends over the area of the image receptor is at most 4 mm at least at the anterior and lateral sides of the housing.

16. The image sensor of claim 15 wherein the width of an inactive rim where the housing extends over the area of the image receptor is at most 2.5 mm at least at the anterior and lateral sides of the housing.

17. The image sensor of claim 15 wherein a minimum height of the housing at the depression, as measured against the back side of the embedded image receptor, is between about 0.5 mm and about 3 mm, and in that the maximum height of the housing at the elevated region, as measured against the back side of the embedded image receptor, is larger than the minimum height by at least 30%.

18. The image sensor of claim 1, wherein a minimum height of the housing at the depression, as measured against the back side of the embedded image receptor, is 0.5 mm-3 mm, and a maximum height of the housing at the elevated region, as measured against the back side of the embedded image receptor, is larger than the minimum height ($h_D$) by at least 30% and preferably by at least 100%.

19. The image sensor of claim 18 wherein the maximum height of the housing at the elevated region, as measured against the back side of the embedded image receptor, is larger than the minimum height by at least 100%.

20. A positioning device for positioning an image sensor in the mouth of a patient for dental intraoral radiography, the positioning device comprising:
   a bite block and a basket;
   the basket comprising a holding member and at least one side bracket;
   the basket is adapted for receiving an image sensor; the image sensor comprising:
      a housing having a front side, a back side, a posterior side, an anterior side, and two lateral sides;
      a cable connection dome arranged on the back side of the housing with a cable outlet towards the posterior side of the housing; and
      the back side of the housing has a depression at least in a region between the cable connection dome and the anterior side of the housing, wherein the depression falls short of reaching the anterior side of the housing such that an elevated region is formed between the depression and at least the anterior side of the housing; and
   wherein the holding member is formed to at least partially rest in the depression and engage with at least one of the cable connection dome and the elevated region when the image sensor is inserted into the basket.

* * * * *

UNITED STATES PATENT AND TRADEMARK OFFICE
CERTIFICATE OF CORRECTION

PATENT NO. : 7,281,847 B2  Page 1 of 1
APPLICATION NO. : 11/196172
DATED : October 16, 2007
INVENTOR(S) : Kokkaliaris et al.

It is certified that error appears in the above-identified patent and that said Letters Patent is hereby corrected as shown below:

Col. 10, Line 3, delete the text "and preferably by at least 100%".

Signed and Sealed this

Seventeenth Day of November, 2009

David J. Kappos
*Director of the United States Patent and Trademark Office*